United States Patent [19]

Schreinemakers

[11] Patent Number: 5,018,972
[45] Date of Patent: May 28, 1991

[54] CORRECTING ARTICULATION DEFECT IN DENTATE HUMAN JAW

[76] Inventor: Josephus Schreinemakers, Oranje Nassaulaann 12, 6026 Maarheeze, Netherlands

[21] Appl. No.: 471,211

[22] Filed: Jan. 26, 1990

[51] Int. Cl.$^5$ .......................... A61C 5/00; A61C 11/00
[52] U.S. Cl. ..................................... 433/215; 433/213
[58] Field of Search ................. 433/215, 229, 37, 213, 433/72; 33/513, 514

[56] References Cited

U.S. PATENT DOCUMENTS

| | | | |
|---|---|---|---|
| 2,040,835 | 5/1936 | Cubbage | 33/513 |
| 2,685,137 | 8/1954 | Thompson | 33/514 |

*Primary Examiner*—John J. Wilson
*Assistant Examiner*—Cindy A. Cherichetti
*Attorney, Agent, or Firm*—Herbert Dubno

[57] ABSTRACT

A model of a maxilla is marked with the location of the patient's lip line and with the location of the patient's ear-nose plane. Then the incisor portion of the model is shaped to have a lower edge lying on the location of the lip line. A calibration plate having a posterior ridge engaging the tuberosity portion of the model, an anterior part engaging the shaped incisor portion of the model, and sides formed with slots aligned with the molar portions of the model is then positioned on the model. The plate extends substantially parallel to the ear-nose plane from shaped front of the model. The slots are filled around the molar portions of the model with wax and a mold fork is fitted flat to the underside of the calibration plate underneath the slots with the compound adhering to the mold fork. Thereafter the fork and the compound are separated from the plate and model and are fitted to the patient. The relative angular orientation between the fork and the patient's ear-nose plane is ascertained and if the fork and plane are not substantially parallel more compound and a different calibration plate is tried, but if the fork and plane are substantially parallel another plate having the same dimensions and ridge height as the plate used with the parallel-lying fork but not formed with slot is selected from the set of calibration plates. Finally the model is ground down using the unslotted plate as a template.

8 Claims, 3 Drawing Sheets

CORRECTING ARTICULATION DEFECT IN DENTATE HUMAN JAW

FIELD OF THE INVENTION

The present invention relates to the correction of a joint or articulation defect in a dentate human jaw. More particularly this invention concerns a method of and tools for making such an adjustment.

BACKGROUND OF THE INVENTION

In a standard procedure for correcting a bite articulation defect in a dentate human jaw, impressions are taken of the maxilla and mandible, that is the upper and lower jaws, and positive models are prepared. Each model has portions corresponding not only to the front incisor, canine, and side molar regions of the patient's teeth, but also portions corresponding to the maxillary and mandibular tuberosities, that is the bony protuberances behind the third molars. A calibration plate is then used to work on the models thus produced in order to reset the so-called articulation or chewing plane.

An articulation defect is defined relative to this joint plane which itself is defined in the front by the lip line of the patient and in the rear by the jaw joint. This joint plane should be parallel to a plane defined by the centers of the ear holes in the rear and the bottom edges of the sides of the nose in the front.

Misalignments of the joint plane can result from teeth having been removed from the upper or lower jaws and the teeth in the opposing jaw shifting complementarily out. In the long run such a joint misalignment can result in considerable problems. Thus it is standard to fit crowns or bridges to patients who have or might develop such a joint-plane misalignment.

Normally the existence of a joint-plane misalignment is determined by visual examination of the model. It is also known to use a so-called articulator in which the model is mounted to try out solutions to the joint problem. Calibration plates are used which follow the uneven contours defined by the prominences of the teeth of the model.

The known method which uses an articulator nonetheless makes it very difficult to transfer any measurements to the patient accurately. Due to the inability to transfer these measurements to the natural teeth of the patient it is relatively difficult to guarantee good long-term results. This is particularly true when the patient is being fitted with a bridge, crown, or the like and it is necessary to determine whether there is any articulation defect and correct it. Typically marking paper is used to leave traces where the teeth meet, but this procedure is not highly accurate.

OBJECTS OF THE INVENTION

It is therefore an object of the present invention to provide an improved method of preparing for correcting an articulation defect in a dentate human jaw.

Another object is the provision of such an improved method of preparing for correcting an articulation defect in a dentate human jaw which overcomes the above-given disadvantages, that is which is simple and highly accurate.

SUMMARY OF THE INVENTION

A preparation method for correcting a bite-articulation defect in a human patient according to the invention comprises first making a positive model of a dentate human maxilla including the tuberosity thereof and of the respective mandible. Thus each model has portions corresponding to the patient's incisors, molars, and tuberosities. The front of the maxilla model is marked with the location of the patient's lip line and on the back it is marked with the location of the patient's ear-nose plane. Then the incisor portion of the maxilla model is shaped to have a lower edge lying on the location of the lip line. A calibration plate having a posterior ridge engaging the tuberosity portion of the maxilla model, an anterior part engaging the shaped incisor portion of the maxilla model, and sides formed with slots aligned with the molar portions of the maxilla model is then positioned on the maxilla model. The plate is selected from a set of plates of different ridge heights such that the slotted plate extends substantially parallel to the ear-nose plane from the shaped front of the maxilla model. The side slots are filled around the molar portions of the maxilla model with mold-making compound, typically wax, and a mold fork is fitted flat to the underside of the calibration plate underneath the slots with the compound adhering to the mold fork. Thereafter the fork and the compound are separated from the plate and maxilla model and are fitted to the patient. The relative angular orientation between the fork and the patient's ear-nose plane is ascertained and if the fork and plane are not substantially parallel more compound and a different calibration plate is tried, but if the fork and plane are substantially parallel another plate having the same dimensions and ridge height as the plate used with the parallel-lying fork but not formed with a slot is selected from the set of calibration plates. Finally the maxilla model is ground down using the unslotted plate as a template.

Subsequently the teeth of the patient can be ground down or built up to correspond to the model, thereby eliminating the articulation defect. It is also possible after grinding down the model to insert between the mandible and maxilla models a synthetic-resin pattern which can subsequently be inserted into the mouth of the patient for use in correcting the teeth therein. It is understood that in accordance with this invention corrective grinding is carried out on the side teeth, that is the molars and premolars. Furthermore the steps of this invention are repeated with the mandible model after being carried out on maxilla model.

A kit for carrying out the method of this invention therefore comprises a set of slotted calibration plates of different ridge heights and a set of unslotted calibration plates of different ridge heights and each of dimensions corresponding to a respective one of the slotted plates. The slotted and unsloted plates of each set according to this invention are graduated in accordance with jaw size and the ridge heights vary from plate to plate within the set by between 1mm and 2mm, with the shortest ridge 1mm high and the tallest one 12mm high. The slotted plates are set in the model parallel to the ear-nose plane as described above after the model is marked. Then the slots are filled with wax and the bite-mold fork is fitted to the plate. This fork with the impression is inserted in the patients to take the occlusal surfaces of the natural teeth so as to verify parallelism with ear-nose plane which, as mentioned above, runs parallel to the articulation plane.

Several ways can be employed to ensure that the calibration plate is parallel to the ear-nose plane on the upper- or lower-jaw model. The above-mentioned mold fork can be used in a method where so much compound is packed into the slots that it flows out and also fills this fork, or even is inserted thereinto by means of the fork which itself has parallel upper and lower surfaces and lies flatly against the planar bottom face of the calibration plate. Then when the fork is fitted to the patient it will run parallel to the ear-nose plane if the calibration plate itself was properly positioned. Once thus determined the ear-nose plane can be marked with a pencil on the model, or at least a plane parallel thereto can be marked on the model. It is also possible to try out different calibration plates until the right one for the ear-nose plane is determined.

The method according to this invention therefore introduces into the determination of a joint-plane error a new reference point, namely the desired orientation of the calibration plate which is determined by grinding down the teeth on the model. Thus the invention recognizes that on the one hand supporting the calibration plate at one end on the tuberosity regions of the models by the plate ridge and at the other end on at the lip line produces the ideal articulation plane for the patient. This allows one to ascertain relatively easily just where articulation defects lie so that same can be eliminated, either by grinding down or building up the teeth.

Thus according to the invention the slotted and unslotted calibration plates have a curved upper surface whose curvature closely corresponds to the curvature of the upper prominences of the occlusal surfaces of the molars and premolars. An imaginary forward extension of this surface corresponds to the lip line regardless of the position of the front teeth. This means that the lip line serves as an orientation point for the front end of the calibration plate. A known law states that the ear-nose plane, the so-called Campers plane, extends parallel to the articulation plane. The curvature of the calibration plate and of the articulation plane are identical, both having in the posterior region a distinct curvature and in the region of the second and third molars an increased upward curvature. This latter curvature in the region of the second and third molars is disregarded in determining the parallelism between the articulation plane and the ear-nose plane. This disregarding is possible in that lateral edges on the rear side of the calibration plates extend in the sagittal region before the premolars and first rollers straight back. The position of this straight portion is according to this invention transferred to the mold fork. Subsequently the mouth of the patient is used to test if indeed the mold fork does extend parallel to the ear-nose plane.

The distance between the highest point of the tuberosities and the occlusal surface of the nearest molar lies between 1mm and 12mm, depending on the patient. Thus for each individual a matched pair of slotted and unslotted plates, that is each having the same dimensions and ridge heights, allows the ridge to lie in the middle of the tuberosities with the plate just touching the occlusal surface of the rearmost molar and the outer edge of the front incisor.

DESCRIPTION OF THE DRAWING

The above and other objects, features, and advantages will become more readily apparent from the following, reference being made to the accompanying drawing in which.

SPECIFIC DESCRIPTION

Figure 1:
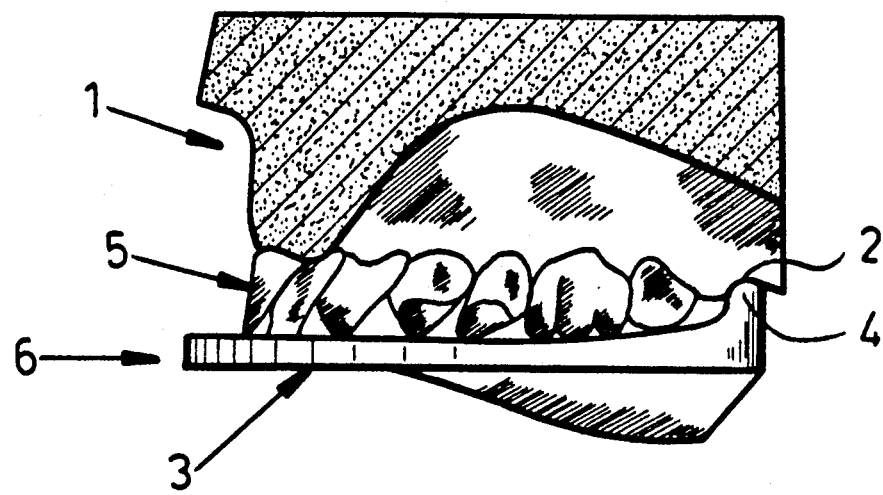
FIG. 1 is a vertical section through a maxilla model fitted with an unslotted calibration plate according to this invention.
Figure 2:
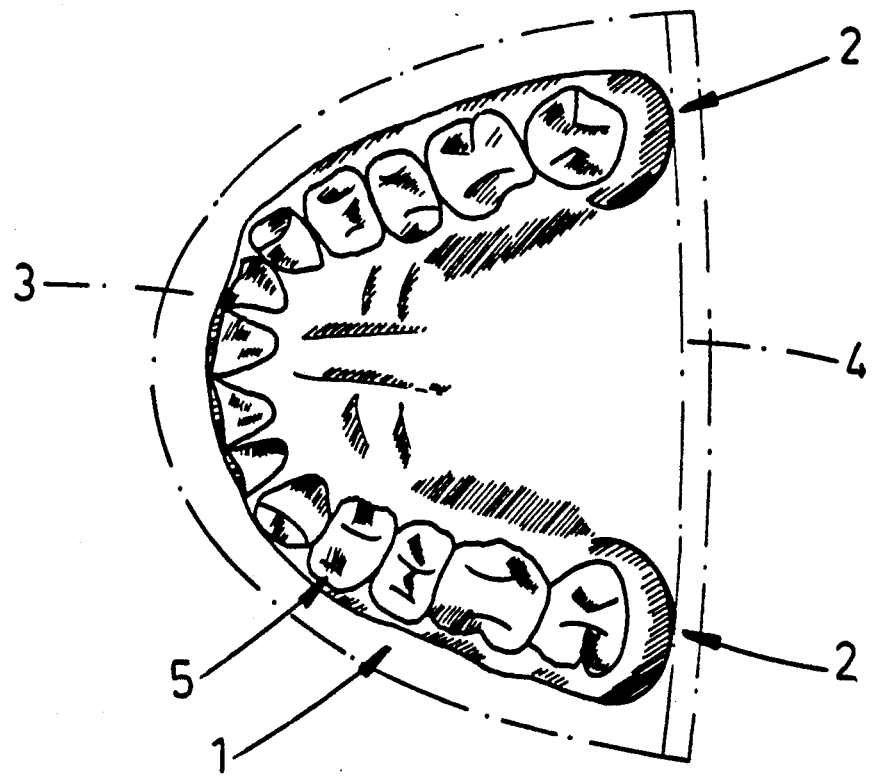
FIG. 2 is a bottom view of the model according to FIG. 1.

As seen in FIG. 1 a positive model 1 of a dentate human maxilla, which is made as is normal by taking a negative impression with wax or the like and then filling the impression with plaster or the like, has a region 2 conforming to the maxillary tuberosity. An unslotted calibration plate 3 has a rear ridge 4 engaging the tuberosities 2 and a front portion engaging upward against the lower edge of the front incisors 5, which lower edge has been ground down or built up to lie level with the patient's lip line 6.

Figure 3:
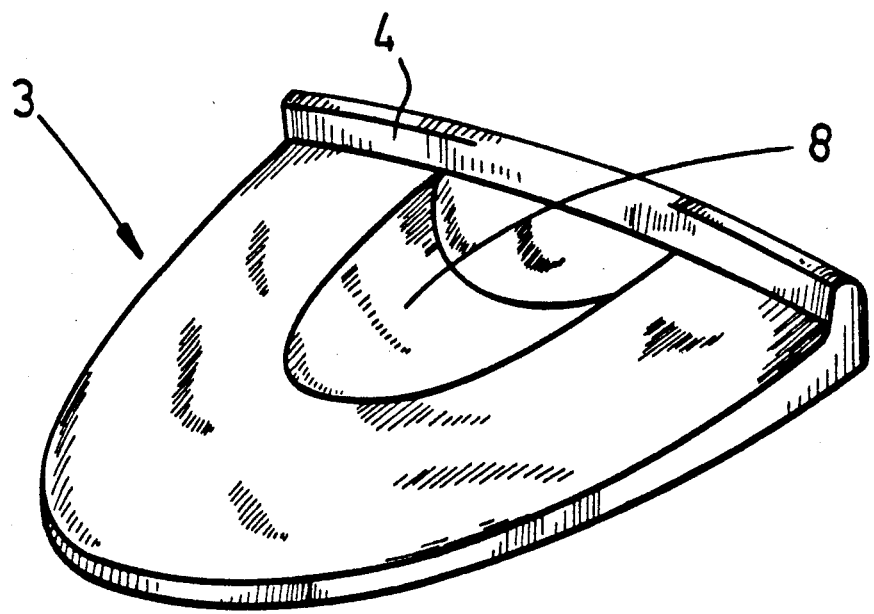
FIGS. 3 and 4 are perspective views of a pair of matched upper-jaw calibration plates.

FIG. 3 shows how the plate 3 is generally flat with a downwardly directed and upwardly concave dome 8. This plate 3 belongs to a set of such plates wherein the height of the ridge 4 increases by 1mm to 2mm between succeeding plates in the series.

Figure 4:
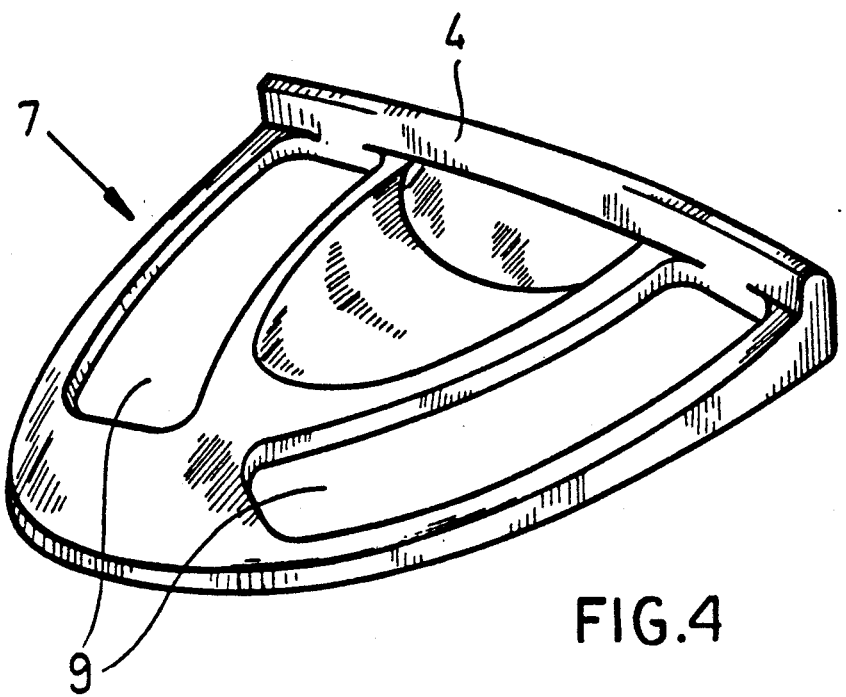
Figure 5:
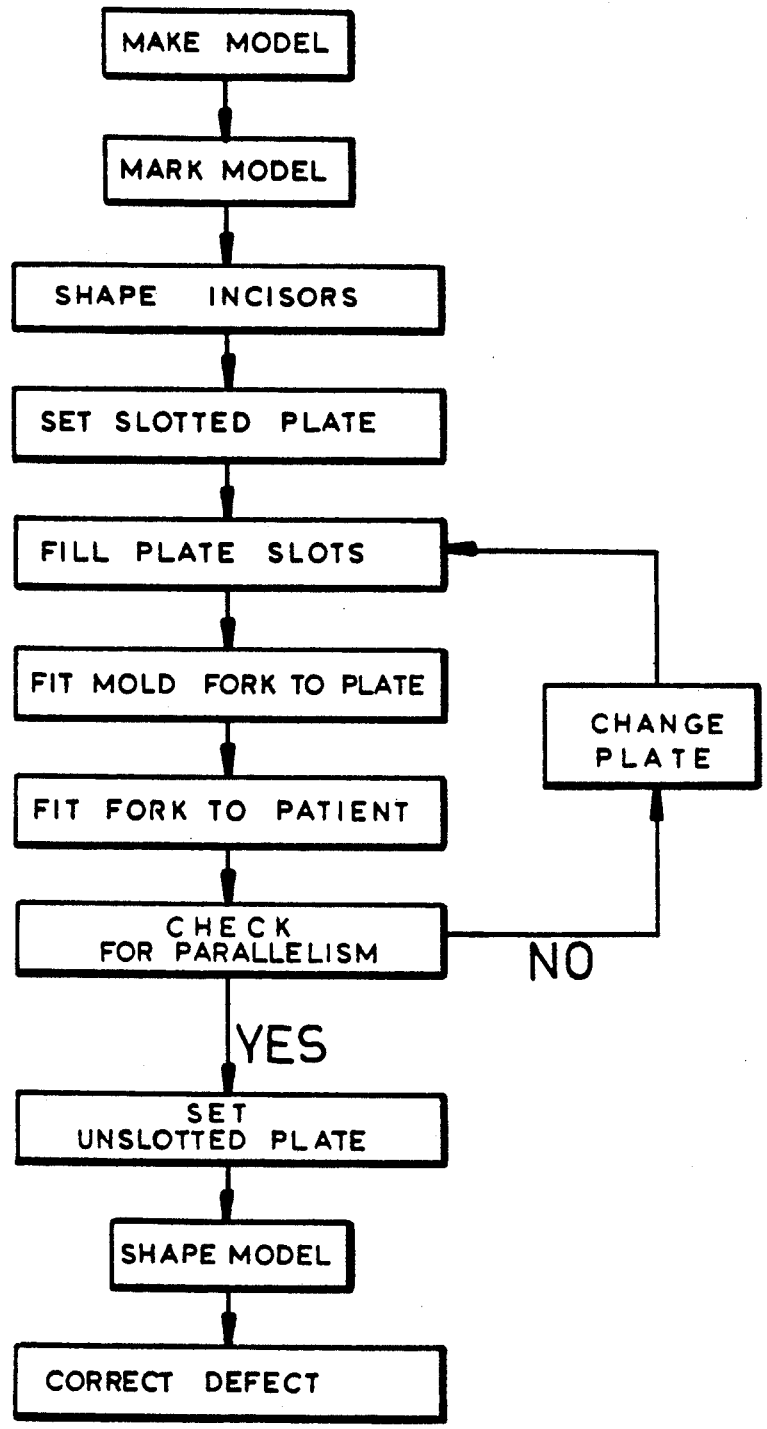
FIG. 5 is a block diagram describing the steps of the method of this invention.

In FIG. 4 a plate 7 is shown having an identical such ridge 4, but formed with slots 9 through which the premolars and molars can extend. In all other respects this plate 7 is identical to the plate 3 of FIG. 3.

I claim:

1. A preparation method for correcting a bite-articulation defect in a human patient, the method comprising the steps of sequentially:
    a) making a positive model of a dentate human maxilla including the tuberosity thereof and of the respective mandible, whereby the maxilla model is formed with portions corresponding to the patient's incisors, molars, and tuberosities;
    b) marking on the front of the maxilla model the location of the patient's lip line and on the back of the maxilla model the location of the patient's ear-nose plane;
    c) shaping the incisor portion of the maxilla model to have a lower edge lying on the location of the lip line;
    d) positioning on the maxilla model a calibration plate having
        a posterior ridge engaging the tuberosity portion of the maxilla model,
        an anterior part engaging the shaped incisor portion of the maxilla model, and
        sides formed with slots aligned with the molar portions of the maxilla model,
    the plate being selected from a set of plates of different ridge heights such that the slotted plate extends substantially parallel to the ear-nose plane from shaped front of the maxilla model;
    e) filling the side slots around the molar portions of the maxilla model with mold-making compound;
    f) fitting a mold fork flat to the underside of the calibration plate underneath the slots with the compound adhering to the mold fork;
    g) separating the fork and the compound from the plate and maxilla model and fitting the fork and compound to the patient;
    h) ascertaining the relative angular orientation between the fork and the patient's ear-nose plane and
    h') if the fork and plane are not substantially parallel repeating steps e), f), and g) with more compound and a different calibration plate, h") if the fork and plane are substantially parallel selecting from the set of calibration plates another plate having the same dimensions and ridge height as the plate used with the parallel-lying fork but not formed with slots; and i) grinding down the maxilla model using the plate unslotted plate of step h") as a template.

2. The method defined in claim 1 wherein steps b) through i) are repeated with the mandible model after being carried out on maxilla model.

3. The method defined in claim 1 wherein the slotted plates of each set are graduated in accordance with jaw size and the ridge heights vary from plate to plate within the set by between 1mm and 2mm.

4. The method defined in claim 1 wherein the unslotted plates of each set are graduated in accordance with jaw size and the ridge heights vary from plate to plate within the set by between 1mm and 2mm.

5. The method according to claim 1 characterized in that a set of auxiliary calibration plate and a set of main calibration plates are used which correspond to one another except with respect to the impression formations, the tuberosity ridges within the plate set being of graduated sizes, whereby by trial-and-error selection the described parallelism with the ear-nose plane can be obtained.

6. The method defined in claim 1 wherein the tuberosity ridges vary from plate to plate within the set of plates by between 1mm to 2mm.

7. The method defined in claim 1 wherein steps b) through i) are sequentially carried out on the model of the mandible.

8. A method of preparation for elimination of an articulation defect in a dentate human jaw
wherein an impression is taken from the dentate maxilla including the tuberosity thereof as well as of the dentate mandible of a patient and a model of the jaw with the tuberosities is prepared based on the impression of the maxilla and mandible,
and wherein the model is worked with the aid of a calibration plate, characterized in that:

a) the level of the lip line as well as of the ear-nose plane is determined on the patient and is marked on the model of the maxilla;

b) the incisors of the maxilla model are ground down or built up in accordance with the marking of the lip line so that the lower edge of the incisors corresponds to the lip line;

c) an auxiliary calibration plate selected from a set of graduated-size such calibration plates is set on the maxilla model prepared according to step b) parallel to the ear-nose plane,
the auxiliary calibration plate having in the region of the side teeth impression formations which the side teeth extend into and the auxiliary calibration plate having on its pharyngeal edge a tuberosity ridge which extends up to the respective tuberosity,
whereby the auxiliary calibration plate engages on the prepared incisors and with the tuberosity ridge on the tuberosity so as to establish the desired orientation for the articulation plane, d) the impression formations on the auxiliary calibration plate are filled around the respective teeth with wax and a bite fork is adhered to the free wax surface parallel to the lateral edges of the auxiliary calibration plate;

e) the bite fork with the wax is inserted into the mouth of the patient and the wax impressions are set on the teeth and if the bite fork is not parallel to the ear-nose plane steps c) and d) are repeated with an auxiliary calibration plate that is a better fit until the desired parallelism between the ear-nose plane and the auxiliary calibration plate is obtained;

f) subsequently a main calibration plate is selected from a set of main calibration plates corresponding to the set of auxiliary calibration plates which has a tuberosity ridge corresponding to that of the auxiliary calibration plate and the model is ground down using this main calibratior plate so as to eliminate the articulation defect on the model.

* * * * *